(12) United States Patent
Inoue et al.

(10) Patent No.: US 11,517,502 B2
(45) Date of Patent: Dec. 6, 2022

(54) CARDIOPULMONARY RESUSCITATION ASSISTING APPARATUS

(71) Applicant: NIHON KOHDEN CORPORATION, Tokyo (JP)

(72) Inventors: Jumpei Inoue, Tokorozawa (JP); Tsutomu Wakabayashi, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 861 days.

(21) Appl. No.: 16/464,460

(22) PCT Filed: Nov. 27, 2017

(86) PCT No.: PCT/JP2017/042392
§ 371 (c)(1),
(2) Date: May 28, 2019

(87) PCT Pub. No.: WO2018/101203
PCT Pub. Date: Jun. 7, 2018

(65) Prior Publication Data
US 2019/0314241 A1  Oct. 17, 2019

(30) Foreign Application Priority Data
Nov. 29, 2016 (JP) .............................. JP2016-231282

(51) Int. Cl.
*A61H 31/00* (2006.01)
*G16H 20/30* (2018.01)
*G16H 40/63* (2018.01)

(52) U.S. Cl.
CPC ......... *A61H 31/005* (2013.01); *A61H 31/007* (2013.01); *G16H 20/30* (2018.01); *G16H 40/63* (2018.01); *A61H 2201/5079* (2013.01)

(58) Field of Classification Search
CPC .... A61H 31/00; A61H 31/005; A61H 31/007; A61H 2201/5079; G16H 20/30; G16H 40/63
See application file for complete search history.

(56) References Cited

U.S. PATENT DOCUMENTS

| | | | |
|---|---|---|---|
| 2004/0082888 | A1 | 4/2004 | Palazzolo et al. |
| 2004/0210170 | A1 | 10/2004 | Palazzolo et al. |

(Continued)

FOREIGN PATENT DOCUMENTS

| | | |
|---|---|---|
| JP | 2006-503659 A | 2/2006 |
| JP | 5508545 B2 | 6/2014 |
| WO | 2012-073900 A1 | 6/2012 |

OTHER PUBLICATIONS

International Search Report Issued in Patent Application No. PCT/JP2017/042392 dated Feb. 22, 2018.

(Continued)

*Primary Examiner* — Timothy A Musselman
(74) *Attorney, Agent, or Firm* — Pearne & Gordon LLP

(57) ABSTRACT

A cardiopulmonary resuscitation assisting apparatus including: an acceleration sensor (13); a magnetic sensor (19); a first calculation section (233A) which obtains a relational expression (N) between a compression depth Da and the coil-to-coil distance AD; a determination section (234) which differentiates the relational expression (N) with respect to an output value of the magnetic sensor (19) and compares a resulting differentiated value of the relational expression (N) with a predetermined threshold to thereby determine whether notification for assistance of cardiopulmonary resuscitation is necessary or not; and a voice generating section (25) which performs the notification for assistance of cardiopulmonary resuscitation.

2 Claims, 6 Drawing Sheets

(56) References Cited

U.S. PATENT DOCUMENTS

| | | |
|---|---|---|
| 2004/0210171 A1 | 10/2004 | Palazzolo et al. |
| 2004/0210172 A1 | 10/2004 | Palazzolo et al. |
| 2007/0010764 A1 | 1/2007 | Palazzolo et al. |
| 2008/0300517 A1 | 12/2008 | Nysaether |
| 2009/0112135 A1 | 4/2009 | Palazzolo et al. |
| 2012/0004582 A1 | 1/2012 | Palazzolo et al. |
| 2013/0060172 A1 | 3/2013 | Palazzolo et al. |
| 2013/0060173 A1 | 3/2013 | Palazzolo et al. |
| 2013/0226049 A1 | 8/2013 | Kandori et al. |
| 2014/0276131 A1* | 9/2014 | Geheb ................ A61B 5/6823 600/533 |
| 2017/0087053 A1 | 3/2017 | Palazzolo et al. |

OTHER PUBLICATIONS

Written Opinion Issued in Patent Application No. PCT/JP2017/042392 dated Feb. 22, 2018.

Tomlinson, A.E., et al., "Compression force-depth relationship during out-of-hospital cardiopulmonary resuscitation", Elsevier Clinical Paper, Resuscitation (2007), vol. 72, pp. 364-370.

Japanese Office Action issued in Japanese Patent Application No. 2016-231282 dated Sep. 1, 2020.

* cited by examiner

CARDIOPULMONARY RESUSCITATION ASSISTING APPARATUS

TECHNICAL FIELD

The present invention relates to a cardiopulmonary resuscitation assisting apparatus.

BACKGROUND ART

CPR (CardioPulmonary Resuscitation) is an important manual operation in emergency medical care. Adequacy of the CPR may affect life and death of a rescuee (patient). When the CPR is performed, a rescuer compresses the sternum of the chest of the patient. Thus, the sternal compression can be performed in place of the patient's heart to circulate blood all over the patient's living body.

For example, according to "JRC Resuscitation Guideline 2015 (Japan Resuscitation Council)", it is recommended to perform manual sternal compression on an adult of normal physique to reach a depth of about 5 cm (or a depth of one third of a thickness of the chest in the case of a child) while avoiding excessive compression exceeding 6 cm.

It is necessary to make further studies about a relation between the compression depth and an external injury, and further about how the relation is affected by body or chest size, chest wall compliance, and a difference between adults and children. Further, it is also necessary to make further studies about a relation of interaction between a pace and the depth of the sternal compression.

In order to guide a rescuer during CPR, there have been developed apparatuses each placed between the chest of a rescuee and hands of the rescuer to assist sternal compression. Each of the apparatuses detects whether adequate force is applied to the chest with an adequately depth and at an adequate time interval, and gives appropriate notification ("force or compression depth is insufficient", "compression timing is too late", etc.) to the rescuer in accordance with the detection.

For example, a background-art apparatus has an acceleration sensor for calculation of a compression depth of sternal compression using a physical law that second-order integration of acceleration is a distance. However, the compression depth obtained from the second-order integration of the acceleration contains lots of error components due to unintentional vibration etc. In order to reduce the influence of the error components caused by the vibration etc. to thereby improve accuracy of the compression depth, a configuration which uses an average value of compression depths in a plurality of compression operations is therefore conceivable. In this configuration, however, a compression depth that is suddenly changed cannot be calculated accurately when such a sudden change in compression depth appears in one of the compression operations.

To solve this problem, a method for physically modeling the chest of a patient to calculate a compression depth has been proposed (see Patent Literature 1).

CITATION LIST

Patent Literature

PTL 1: Japanese Patent No. 5508545

Non Patent Literature

NPL 1: A. E. Tomlinson, et. al, "Compression force-depth relationship during out-of-hospital cardiopulmonary resuscitation", ELSEVIER 2006, pp 364-370.

SUMMARY OF INVENTION

Technical Problem

The recommendation in the aforementioned guideline is set on the assumption that the patient is an adult of normal physique. However, due to individual differences in physique among patients, there is a possibility that, for example, a compression displacement of 5 cm is adequate for some patients but not sufficient for other patients. When the compression displacement is used thus as an index of the sternal compression, it is difficult to guide the rescuer to perform sternal compression adequate for every patient.

An object of the invention is to provide a cardiopulmonary resuscitation assisting apparatus capable of guiding a rescuer to perform sternal compression adequate for every patient.

Solution to Problem

The cardiopulmonary resuscitation assisting apparatus according to the invention is a cardiopulmonary resuscitation assisting apparatus that assists cardiopulmonary resuscitation when the cardiopulmonary resuscitation is performed on a target, the apparatus including:

a first sensor which detects acceleration of movement of a compressed part of the target due to compression operation;

a second sensor which outputs information corresponding to a magnitude of compression on the compressed part of the target due to the compression operation;

a first calculation section which obtains a relational expression between a compression depth calculated based on second-order integration of the acceleration information acquired from the first sensor, and the information corresponding to the magnitude of the compression acquired from the second sensor;

a determination section which differentiates the relational expression with respect to an output value of the second sensor and compares a resulting differentiated value of the relational expression with a predetermined threshold to thereby determine whether notification for assistance of cardiopulmonary resuscitation is necessary or not; and a notification section which performs the notification for assistance of cardiopulmonary resuscitation when determination is made by the determination section that the notification is necessary.

According to the cardiopulmonary resuscitation assisting apparatus having the aforementioned configuration, determination as to whether the notification for assistance of cardiopulmonary resuscitation is necessary or not is made using a rate of change (differentiated value) of the relational expression between the compression depth and the information corresponding to the magnitude of the compression. For example, when the rate of change becomes gentle, this means that it is difficult to perform any more compression. It is therefore considered that the sternum of the target (patient) is compressed with a sufficient compression depth. In addition, when the rate of change is not smaller than a predetermined value, this means that there is still a room for more compression. It is therefore considered that the compression depth applied to the target (patient) may be insufficient.

Thus, according to the aforementioned configuration, it is possible to provide the cardiopulmonary resuscitation assisting apparatus which can guide a rescuer to perform sternal compression adequate for every patient when the rate of change (differentiated value) of the aforementioned relational expression is used.

Advantageous Effects of Invention

According to the invention, it is possible to provide a cardiopulmonary resuscitation assisting apparatus capable of guiding a rescuer to perform sternal compression adequate for every patient.

DESCRIPTION OF EMBODIMENTS

An embodiment of a cardiopulmonary resuscitation assisting apparatus according to the invention will be described below by way of example with reference to the drawings. Incidentally, the invention is not limited to these illustrated examples. The invention is represented by the scope of Claims thereof, and intended to include all changes within the meaning and scope equivalent to the scope of Claims.

Figure 1:
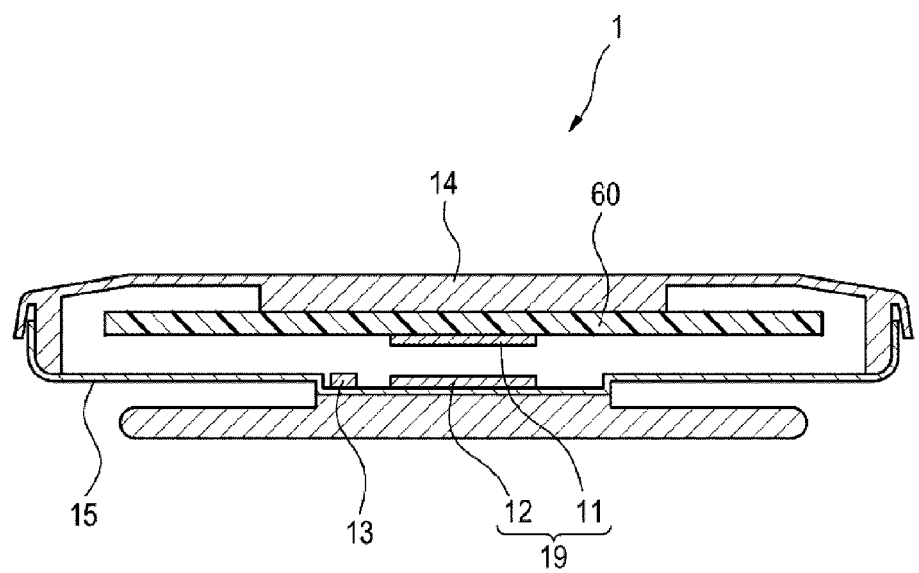
FIG. 1 is a sectional view of a measurement device of a cardiopulmonary resuscitation assisting apparatus according to an embodiment of the invention.
Figure 1:
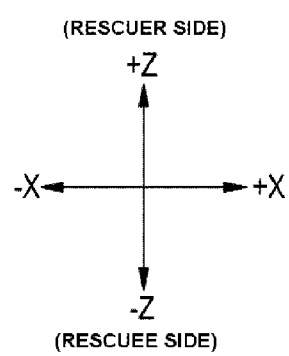

In FIG. 1, the reference sign 1 designates a measurement device of the cardiopulmonary resuscitation assisting apparatus according to the embodiment. The measurement device 1 is a device which is placed between the chest (preferably right above the sternum) of a rescuee and hands of a rescuer to assist sternal compression. Incidentally, the rescuee is a concept including not only a human invalid (or also expressed as patient) but also a mannequin etc. That is, the cardiopulmonary resuscitation assisting apparatus may be used at a scene of real cardiopulmonary resuscitation or may be used at the time of cardiopulmonary resuscitation training. The cardiopulmonary resuscitation assisting apparatus detects compression depths and a number of times of sternal compression using displacements detected by a sensor whenever the chest of the rescuee is pressed and whenever the chest of the rescuee is released from pressing. Therefore, the cardiopulmonary resuscitation assisting apparatus is required to have spring characteristics with which a displacement is generated whenever the chest of the rescuee is pressed.

A housing of the measurement device 1 of the cardiopulmonary resuscitation assisting apparatus includes a fixed section 15 and a movable section 14. The fixed section 15 and the movable section 14 are fitted into each other to thereby form the housing.

In the following description, directional axes (X axis, Z axis) are determined, as shown in FIG. 1. In addition, since a face of the measurement device 1 in a positive direction of the Z axis (+Z direction) makes contact with the rescuer, the +Z direction will be also referred to as "rescuer side". Similarly, since a face of the measurement device 1 in a negative direction of the Z axis (−Z direction) makes contact with the rescuee, the −Z direction will be also referred to as "rescuee side".

The measurement device 1 of the cardiopulmonary resuscitation assisting apparatus is mounted on the chest (preferably right above the sternum) of the rescuee with the fixed section 15 facing downward. The rescuer performs sternal compression to press a planar place of the movable section 14. When the rescuer performs the pressing, pressure is transmitted to the chest of the rescuee from a bottom direction of the fixed section 15. The rescuer who is mostly an adult fixes his/her hands to the measurement device 1 of the cardiopulmonary resuscitation assisting apparatus to perform pressing. Therefore, it is preferable that the measurement device 1 of the cardiopulmonary resuscitation assisting apparatus has a size fitted to the size of an adult's palm.

Here, the sternal compression will be described briefly. Adequacies in (1) the number of times, (2) depth (compression depth) and (3) returning of the sternal compression largely affect a rescue effect of the sternal compression. It has been considered that the number of times of the sternal compression is preferably at least about 100 to 120 times per minute. In addition, as to the compression depth of the sternal compression, it is recommended to manually perform the sternal compression on an adult of normal physique to reach a depth of about 5 cm (or a depth of one third of a thickness of the chest in the case of a child) while avoiding excessive compression exceeding 6 cm. When the compression depth is too small, a massage effect on the heart is insufficient. On the other hand, when the compression depth is too large, there is a fear that the sternum etc. may be broken. In addition, the chest is required to be decompressed sufficiently every time immediately after the compression is performed by manual operation of the rescuer. When the decompression is not sufficient, blood circulation becomes insufficient. The cardiopulmonary resuscitation assisting apparatus measures an actual compression depth and the number of times of compression (a compression rate), and compares these values with indices (not smaller than 5 to 6 cm, 100 to 120 times/minute).

The movable section 14 is a member to which pressure is directly applied by the manual operation of the rescuer, and which is a non-repulsive member (having no spring characteristic). The movable section 14 is physically connected to the fixed section 15 and a printed board 60.

Various circuits and software for detecting and measuring strength of the sternal compression performed by the rescuer and a frequency of the sternal compression are mounted in the printed board 60.

The fixed section 15 is a member (repulsive member) having spring characteristics. In other words, the fixed section 15 is regarded as a spring 16 (see FIG. 3) which is bent in the +Z direction (rescuer side) during pressing of the sternal compression and which is restored toward the −Z direction (rescuee side) during release of the pressing.

The measurement device 1 of the cardiopulmonary resuscitation assisting apparatus has a receiver coil (magnetic field detecting section) 11 which is provided in the movable section 14, and a transmitter coil (magnetic field generating section) 12 which is provided in the fixed section 15. In addition, the measurement device 1 of the cardiopulmonary resuscitation assisting apparatus has an acceleration sensor (first sensor) 13 which is provided in the fixed section 15.

Figure 2:
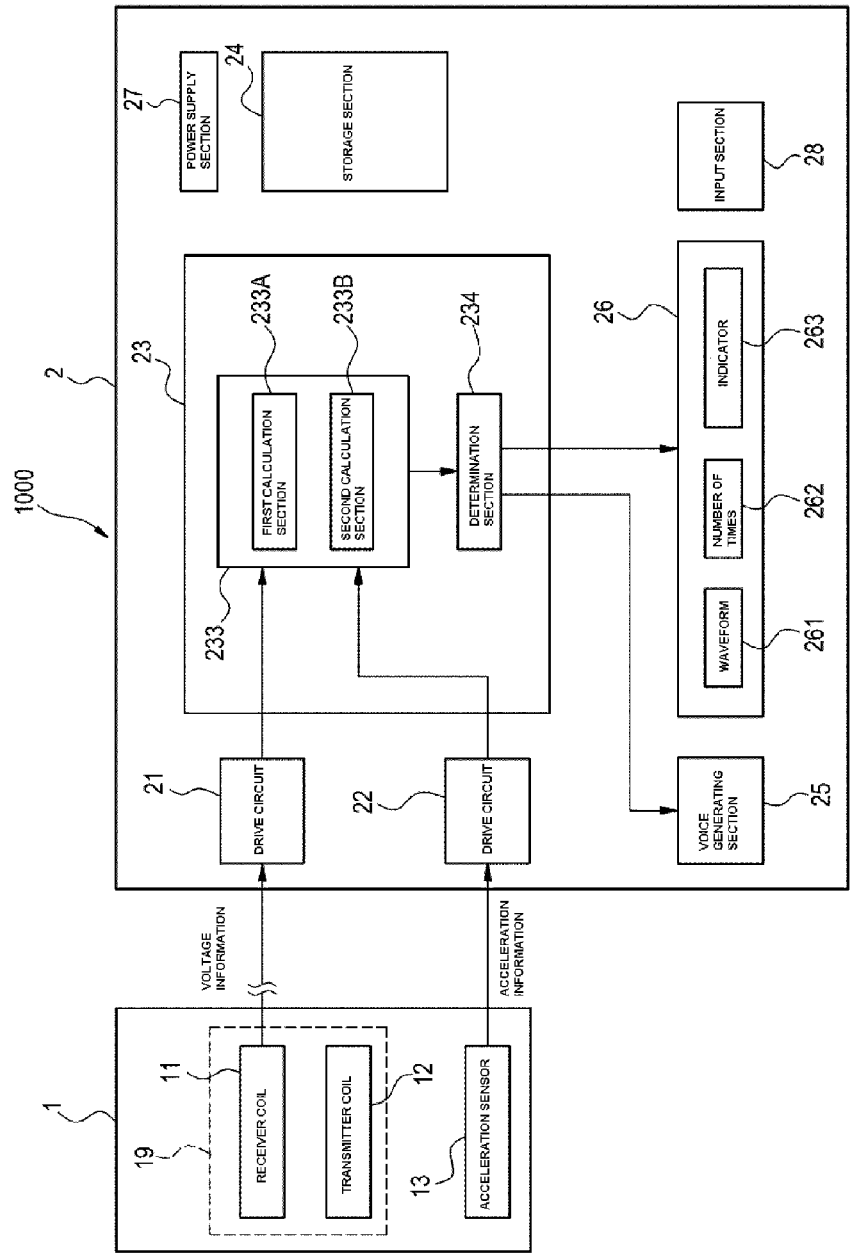
FIG. 2 is a block diagram of an overall configuration of the cardiopulmonary resuscitation assisting apparatus according to the embodiment.

As shown in FIG. 2, the cardiopulmonary resuscitation assisting apparatus is provided with a compression depth calculating device 1000. The compression depth calculating device 1000 is configured to include the measurement device 1 and a calculation device 2.

Figure 3:
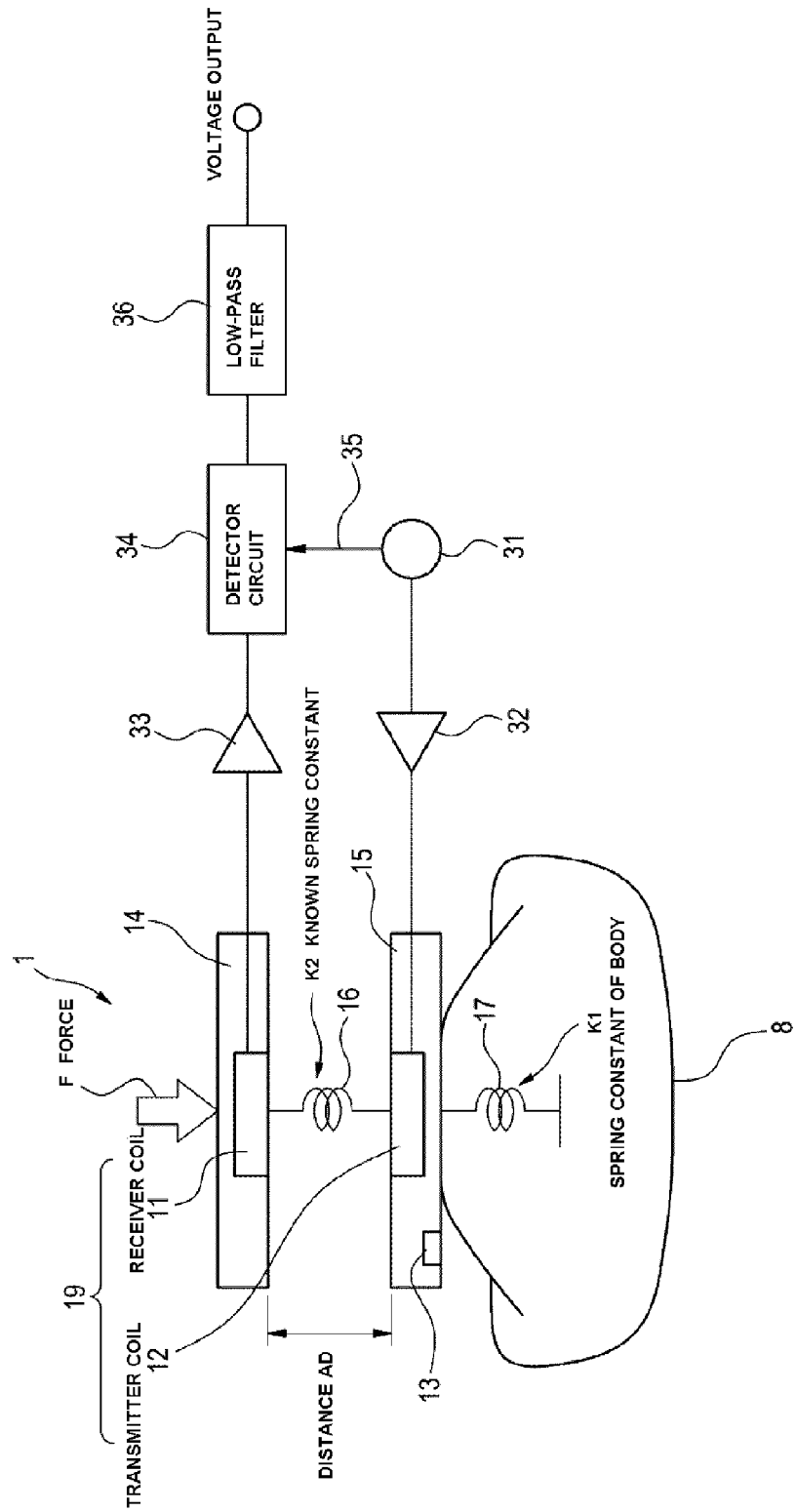
FIG. 3 is a view showing the configuration of the cardiopulmonary resuscitation assisting apparatus etc.

As shown in FIG. 3, the measurement device 1 is configured to include the receiver coil 11 (magnetic field detecting section), the transmitter coil 12 (magnetic field generating section), the acceleration sensor 13, the movable section 14 and the fixed section 15. Here, the spring characteristics of the fixed section 15 are extracted as the spring 16 (elastic body) and clearly stated in the description. Incidentally, the receiver coil 11 and the transmitter coil 12 are combined to be referred to as a magnetic sensor (second sensor) 19.

The transmitter coil 12 and the acceleration sensor 13 are disposed in the fixed section 15. The fixed section 15 is fixed to a body B of the rescuee. For example, a method for disposing the body B on an anti-slipping sheet is considered as a fixation method. Here, the body B has spring characteristics and damper characteristics. Of them, the spring characteristics are dominant. Accordingly, the body B can be approximately regarded as a spring 17 having a spring constant K1. Incidentally, the spring constant K1 may be not lower than secondary.

The receiver coil 11 is disposed in the movable section 14 to be opposed to the transmitter coil 12. The spring 16 made of the fixed section 15 and having a spring constant K2 is disposed between the movable section 14 and the fixed section 15. Incidentally, the fixed section 15 serving as the spring 16 is selected so as to establish a relation K2>K1. Otherwise, when force F of compression is applied to the movable section 14, the spring 16 will contract up to a shortest length and a movable region will be hence limited. Therefore, a role as the magnetic sensor 19 will be spoiled. Incidentally, it is desirable to set a distance between the movable section 14 and the fixed section 15, for example, at about 5 mm.

Next, operations of the magnetic sensor 19 and peripheral components will be described with reference to FIG. 3. First, an AC (alternating current) oscillator 31 creates an AC voltage with a specific frequency (e.g. 20 kHz). The AC voltage is converted into an AC current with the specific frequency by an amplifier 32. The converted AC current flows into the transmitter coil 12. A magnetic field generated by the AC current flowing through the transmitter coil 12 generates an induced electromotive force in the receiver coil 11.

An AC current (having a frequency which is the same as the frequency of the AC voltage created by the AC oscillator 31) occurring in the receiver coil 11 due to the induced electromotive power is amplified by a preamplifier 33. A signal of the amplified AC current is inputted to a detector circuit 34. In the detector circuit 34, the signal of the amplified AC current is detected by the specific frequency created by the AC oscillator 31 or a frequency twice as high as the specific frequency. Therefore, an output of the AC oscillator 31 is introduced as a reference signal 35 into a reference signal input terminal of the detector circuit 34. Incidentally, when a full-wave rectifier circuit is used without using the detector circuit 34 and the reference signal 35, the measurement device 1 may be operated by the circuit. Thus, the size and price of the measurement device 1 can be reduced by the configuration of the full-wave rectifier circuit. After having passed through a low-pass filter 36, voltage information (output signal) from the detector circuit 34 (or the full-wave rectifier circuit) is introduced into a drive circuit 21 (see FIG. 2) of the calculation device 2.

As shown in FIG. 2, the calculation device 2 is a computer device which is configured to include the drive circuit 21, a drive circuit 22, a processing section 23, a storage section 24, a voice generating section (an example of a notification section) 25, a display section 26 (an example of the notification section), a power supply section 27, and an input section 28. In addition, the calculation device 2 may have a communication section for communicating with an external device.

The drive circuit 21 transmits, to the processing section 23, the voltage information received via the low-pass filter 36 (see FIG. 3) etc. from the receiver coil 11 of the measurement device 1.

The drive circuit 22 converts acceleration information received from the acceleration sensor 13 of the measurement device 1 into a voltage, and transmits the converted voltage to the processing section 23.

The processing section 23 is implemented, for example, by a CPU (Central Processing Unit). The processing section 23 is provided with a calculation section 233 and a determination section 234.

The calculation section 233 performs various calculations. The determination section 234 performs various determinations. The calculation section 233 is provided with a first calculation section 233A and a second calculation section 233B. The storage section 24 is a unit which stores various information. The storage section 24 is implemented, for example, by an RAM (Random Access Memory), an ROM (Read Only Memory), an HDD (Hard Disk Drive), or the like. The voice generating section 25 is a unit which generates voice. The voice generating section 25 is implemented, for example, by a speaker. The display section 26 is a unit which performs various displays. The display section 26 is implemented, for example, by an LCD (Liquid Crystal Display) or a CRT (Cathode Ray Tube) display. A waveform 261, a number of times 262, an indicator 263, etc. are displayed on the display section 26. The waveform 261 expresses a state of change of a compression depth with time. The number of times 262 expresses a number of times compression has been performed. The indicator 263 expresses a magnitude of the compression depth. The power supply section 27 is a power supply unit in the calculation device 2. The input section 28 is a unit which is operated by a user in order to input various information. The input section 28 is implemented, for example, by a keyboard, a mouse, a switch, or the like.

During CPR held once, the rescuer performs compression operation, for example, at a frequency of 120 times per minute. On this occasion, it is preferable that the rescuer continuously gives, for example, a constant compression displacement of 5 cm or more to the chest of a patient in each compression operation. However, the compression operation repeated at a constant pace and with constant strength is a considerable load on the rescuer. For this reason, the compression displacement may vary from one compression operation to another. In addition, the rescuer may be taken over by another rescuer in the middle of the manual operation in order to disperse the load. Also in this case, the compression displacement may vary from one compression operation to another.

Thus, it can be fully predicted that the compression displacement may vary from one compression operation to another when the manual operation is actually performed. To solve this problem, there is an increasing demand for a device which can calculate a compression depth accurately even when the compression displacement varies from one compression operation to another.

Figure 4:
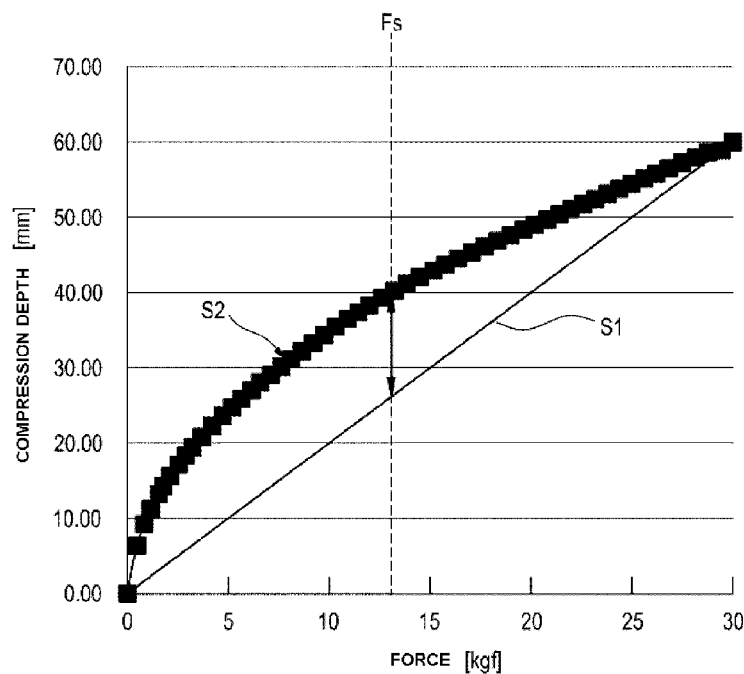
FIG. 4 is a graph showing a relation between compression force and compression depth.

On the other hand, according to the background-art technique in Patent Literature 1, the chest of the rescuee is modeled linearly on the assumption that the spring constant of the chest of the rescuee is fixed. In the linear model, a compression depth can be calculated accurately when the compression depth in each compression operation falls into a fixed range. However, as shown in FIG. 4, in contrast to the linear model in which the compression depth is modeled linearly (as designated by a reference sign S1), an actual chest has a spring constant which can change in accordance with the compression depth to be non-linear (as designated by a reference sign S2). Accordingly, a relation between the compression depth and compression force should be modeled non-linearly.

Figure 5:
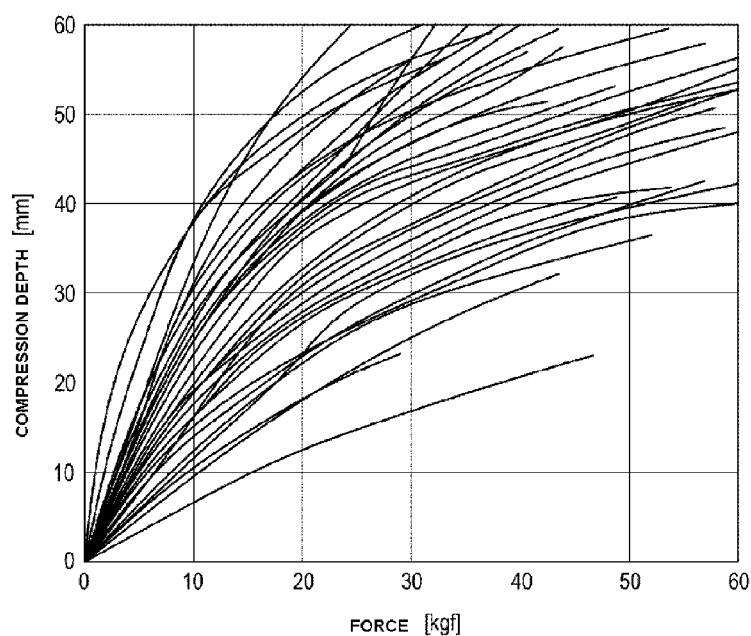
FIG. 5 is a graph showing relations between compression force and compression depth in different rescuees.

The present inventor has recognized that an influence of the linear model of a non-linear chest appears largely particularly in a case where the compression depth changes suddenly in one of a plurality of compression operations, and the influence is not negligible. For example, assume that the compression force is weak (as designated by Fs in FIG. 4). In this case, a large deviation may occur in the compression depth between the linear model S1 and the non-linear model S2. In addition, due to individual differences in physique among patients, the relation between the change of the compression depth and the compression force varies from one patient to another, as shown in FIG. 5.

Therefore, the cardiopulmonary resuscitation assisting apparatus according to the invention assists the rescuer to perform sternal compression adequate for every patient.

A method using the cardiopulmonary resuscitation assisting apparatus to assist the rescuer will be described below.

(Extraction of Relational Expression)

Figure 6:
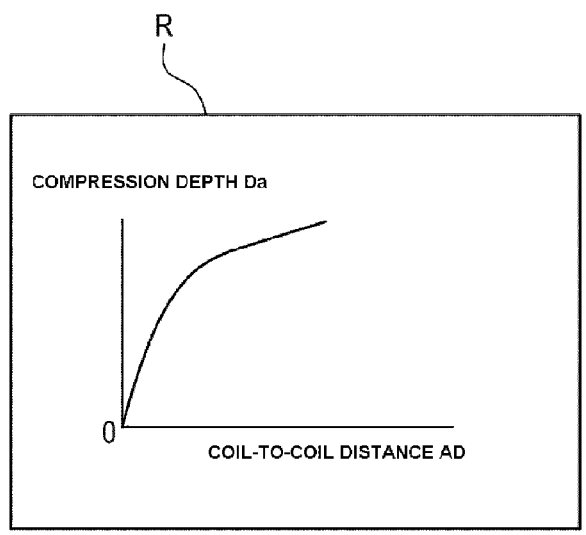
FIG. 6 is a graph showing a correlation between coil-to-coil distance and compression depth.

In the calculation section 233, the first calculation section 233A applies second-order integration to acceleration acquired from the acceleration sensor 13 to calculate a compression depth Da. The first calculation section 233A obtains a relational expression N between the compression depth Da which is calculated based on the second-order integration of the acceleration information acquired from the acceleration sensor 13 and a coil-to-coil distance AD which is a distance between the receiver coil 11 and the transmitter coil 12 acquired from the magnetic sensor 19. The relational expression N is expressed as a mathematical expression of a correlation R (data aggregate including a plurality of variables (two variables in this example)) between the compression depth Da which is calculated based on the second-order integration of the acceleration information acquired from the acceleration sensor 13, and the coil-to-coil distance AD which is the distance between the receiver coil 11 arid the transmitter coil 12 acquired from the magnetic sensor 19, as shown in FIG. 6. Incidentally, the correlation R shows a change amount of the compression depth Da with respect to the coil-to-coil distance AD. The compression depth Da is obtained by applying second-order integration to the acceleration acquired from the acceleration sensor 13.

Since a spring constant of an actual chest changes in accordance with the compression depth, the spring constant of the actual chest may be often non-linear. Incidentally, a spring constant of a linear spring used in a doll for practicing sternal compression may be linear.

Examples of the method for expressing the correlation R as the mathematical expression (relational expression N) include a method for using a least-squares method on collected data to calculate a relational expression, a method for interpolating data between plotted data by linear interpolation etc. to obtain a relational expression, etc.

Figure 7:
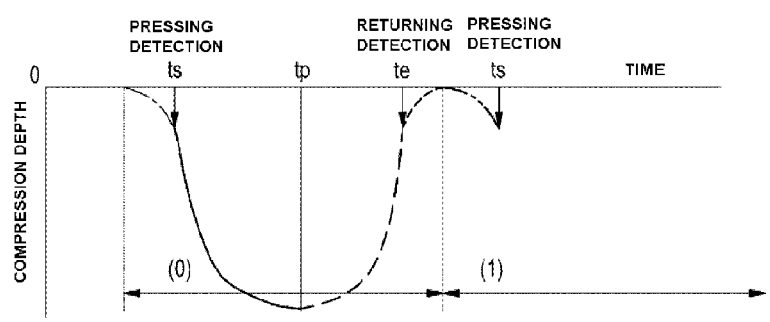
FIG. 7 is a graph showing compression depth during compression operation.

Here, FIG. 7 shows a change of a compression depth of an actual chest when the chest of a rescuee is compressed. In the change of the compression depth, the first calculation section 233A obtains a correlation R between a pressing detection time (ts) and a compression depth peak time (tp) in a section between pressing detection (ts) and returning detection (te) determined based on a change of the coil-to-coil distance AD, and obtains a relational expression N from the correlation R.

(Extraction of Average Expression)

Figure 8:
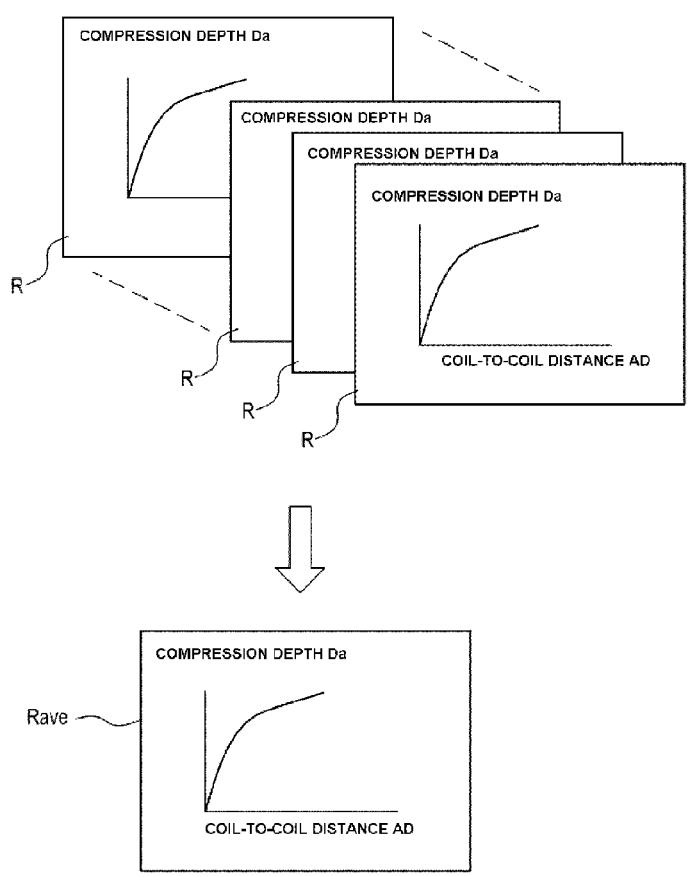
FIG. 8 is a schematic view showing an average correlation obtained from a plurality of correlations.

In the calculation section 233, the second calculation section 233B obtains an average expression Nave which is an average of a plurality of relation expressions N. The average expression Nave is expressed as a mathematical expression of an average correlation Rave which is an average of a plurality of (sixteen in this example) correlations R obtained in the first calculation section 233A, as shown in FIG. 8. Noise may be contained in a second-order integrated value of the acceleration acquired from the acceleration sensor 13. However, since the average expression Nave is obtained from the average correlation Rave which is the average of the plurality of correlations R, the influence of the noise can be reduced.

Here, the second calculation section 233B of the calculation section 233 always obtains an average expression Nave from an average correlation Rave which is an average of a predetermined number of (e.g. sixteen) correlations R immediately before compression operation. When the number of correlations R immediately before the compression operation is smaller than the predetermined number in an early period after the compression start, the second calculation section 233B of the calculation section 233 obtains an average expression Nave from an average correction Rave obtained by averaging the plurality of correlations R smaller in number than the predetermined number.

(Determination about Whether Notification is Necessary or not)

The determination section 234 differentiates the average expression Nave with respect to an output value of the magnetic sensor 19 and compares a resulting differentiated value of the average expression Nave with a predetermined threshold to thereby determine whether notification for assistance of cardiopulmonary resuscitation is necessary or not. Incidentally, the predetermined threshold is a rate of change (inclination) when the depth of the compression applied to the rescuee is adequate. The predetermined threshold is stored in advance in the storage section 24.

When, for example, the rate of change of the differentiated value obtained by differentiating the average expression Nave with respect to the output value of the magnetic sensor 19 is larger by at least a fixed value than a rate of change of the predetermined threshold, it is determined that the compression has not reached an adequate compression depth. On the other hand, when the rate of change of the differentiated value obtained by differentiating the average expression Nave with respect to the output value of the magnetic sensor 19 is smaller by at least the fixed value than the rate of change of the predetermined threshold, it is determined that the compression has exceeded the adequate compression depth. When the differentiated value of the average operation Nave is deviated from the predetermined threshold because the actual compression depth Dr is too large or too small, the determination section 234 determines that notification is necessary.

(Notification to Rescuer)

When determination is made by the determination section 234 that notification is necessary, the voice generating section 25 performs the notification for assistance of cardiopulmonary resuscitation. For example, when determination is made by the determination section 234 that the compression depth Dr is too small, the voice generating section 25 generates voice guidance "Please press more strongly". On the other hand, when determination is made by the determination section 234 that the compression depth Dr is too large, the voice generating section 25 generates voice guidance "Please press more weakly". Incidentally, the aforementioned voice message may be displayed by characters on the display section 26 in addition to or in place of the voice guidance. In addition, attention of people in the surroundings may be drawn by blink speed or color of light through the display section 26 etc. in accordance with a result of the determination.

According to the cardiopulmonary resuscitation assisting apparatus according to the embodiment as described above, determination as to whether notification for assistance of cardiopulmonary resuscitation is necessary or not is made using the rate of change (differentiated value) of the average expression Nave obtained as the average of the plurality of relational expressions N between the compression depth D and the coil-to-coil distance AD which is the information corresponding to the magnitude of the compression. For example, when the rate of change becomes gentle, this means that it is difficult to perform any more compression. It is therefore considered that the sternum of the rescuee who is the target (patient) has been compressed to a sufficient compression depth Dr. In addition, when the rate of change is not smaller than the fixed value, this means that there is still a room for more compression. It is therefore considered that the compression depth Dr applied to the rescuee who is the target (patient) is insufficient.

In addition, for determination as to whether notification is necessary or not, not only the rate of change but also the compression depth may be used so that the determination is made based on a combination of the two parameters. For example, assume that the rate of change is still not smaller than the fixed value in spite of compression performed with a minimum depth of 5 cm. In this case, it may be determined that compression should be performed more deeply, and notification may be therefore performed.

Thus, according to the embodiment, it is possible to provide the cardiopulmonary resuscitation assisting apparatus which can guide the rescuer to perform sternal compression adequate for every patient when the rate of change (differentiated value) of the average expression Nave which is the average of the plurality of relational expressions N is used.

Here, the second-order integrated value of the acceleration acquired from the acceleration sensor 13 contains a lot of noise. According to the embodiment, the influence of the noise can be reduced because the average expression Nave which is the average of the plurality of relational expressions N is used. Therefore, it is possible to guide the rescuer to perform sternal compression adequate for every patient more accurately.

Incidentally, in the aforementioned embodiment, the average expression Nave which is obtained as the average of the plurality of relational expressions N by the second calculation section 232B is used when determination as to whether notification is necessary or not is made by the determination section 234. However, the average expression Nave may not be always used. For example, a relational expression N obtained at the time of previous compression operation may be used when determination as to whether notification is necessary or not is made by the determination section 234. Also in this case, it is possible to guide the rescuer to perform sternal compression adequate for every patient.

Moreover, according to the embodiment, the coil-to-coil distance AD which is distance information between the transmitter coil 12 and the receiver coil 11 can be obtained accurately as the information corresponding to the magnitude of the compression from the magnetic sensor 19. Therefore, reliability as to accuracy of the aforementioned average expression Nave or the relational expression N is also increased. Accordingly, it is possible to guide the rescuer to perform sternal compression adequate for every patient.

The invention is not limited to the aforementioned embodiment and modifications. Modification, improvement, etc. can be made on the invention desirably and suitably. Moreover, the materials, shapes, dimensions, numeral values, forms, numbers, arrangement places, etc. of the respective constituent elements in the aforementioned embodiment are not limited but may be set desirably as long as they can attain the invention.

For example, in FIGS. 6 and 8, the value of the magnetic sensor 19 is indicated on the abscissa and the second-order integrated value (compression depth) of the acceleration sensor 13 is indicated on the ordinate. The invention is not limited to this example. The value of the magnetic sensor 19 may be indicated on the ordinate and the second-order integrated value (compression depth) of the acceleration sensor 13 may be indicated on the abscissa.

The present application is based on Japanese Patent Application No. 2016-231282 filed on Nov. 29, 2016, the contents of which are hereby incorporated by reference.

What is claimed is:

1. A cardiopulmonary resuscitation assisting apparatus which assists cardiopulmonary resuscitation when the cardiopulmonary resuscitation is performed on a target, the apparatus comprising:
   a first sensor which detects acceleration of movement of a compressed part of the target due to compression operation;
   a second sensor which outputs information corresponding to a magnitude of compression on the compressed part of the target due to the compression operation;
   a first calculation section which obtains a relational expression between a compression depth calculated based on second-order integration of the acceleration information acquired from the first sensor, and the information corresponding to the magnitude of the compression acquired from the second sensor;
   a determination section which differentiates the relational expression with respect to an output value of the second sensor and compares a resulting differentiated value of the relational expression with a predetermined threshold to thereby determine whether notification for assistance of cardiopulmonary resuscitation is necessary or not;
a notification section which performs the notification for assistance of cardiopulmonary resuscitation when determination is made by the determination section that the notification is necessary; and
a second calculation section which obtains an average expression which is an average of a plurality of the relation expressions,
wherein the determination section differentiates the average expression with respect to an output value of the second sensor and compares a differentiated value of the average expression with a predetermined threshold to thereby determine whether notification for assistance of cardiopulmonary resuscitation is necessary or not.

2. The cardiopulmonary resuscitation assisting apparatus according to claim 1, wherein:
the second sensor is a magnetic sensor;
the magnetic sensor includes:
a fixed section which is fixed to the compressed part of the target;
a movable section which is provided in an opposed position to the fixed section so as to be movable in a direction of the compression;
a magnetic field generating section which generates a magnetic field; and
a magnetic field detecting section which detects the magnetic field;
the magnetic field generating section is provided in one of the fixed section and the movable section, and the magnetic field detecting section is provided in the other of the fixed section and the movable section;
the first sensor is disposed in the fixed section; and
the magnetic field generating section, the magnetic field detecting section, and the first sensor disposed in the fixed section are arranged side by side in the direction of the compression.

* * * * *

UNITED STATES PATENT AND TRADEMARK OFFICE
CERTIFICATE OF CORRECTION

| | |
|---|---|
| PATENT NO. | : 11,517,502 B2 |
| APPLICATION NO. | : 16/464460 |
| DATED | : December 6, 2022 |
| INVENTOR(S) | : Jumpei Inoue |

It is certified that error appears in the above-identified patent and that said Letters Patent is hereby corrected as shown below:

In the Specification

Column 5, Line 51, "components will he described" should read -- components will be described --

Column 7, Line 62, "11 arid the transmitter" should read -- 11 and the transmitter --

Signed and Sealed this
Twenty-sixth Day of December, 2023

Katherine Kelly Vidal
*Director of the United States Patent and Trademark Office*